United States Patent
El Zoghbi (10) Patent No.: US 11,998,188 B2
(45) Date of Patent: Jun. 4, 2024

(54) SUTURE THREADER FOR BONE PLATE

(71) Applicant: Depuy Synthes Products, Inc., Raynham, MA (US)

(72) Inventor: Gaser El Zoghbi, Rombach (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 358 days.

(21) Appl. No.: 17/552,001

(22) Filed: Dec. 15, 2021

(65) Prior Publication Data

US 2022/0202414 A1 Jun. 30, 2022

Related U.S. Application Data

(60) Provisional application No. 63/131,127, filed on Dec. 28, 2020.

(51) Int. Cl.
| A61B 17/04 | (2006.01) |
| A61B 17/17 | (2006.01) |
| A61B 17/80 | (2006.01) |

(52) U.S. Cl.
CPC ...... *A61B 17/0482* (2013.01); *A61B 17/0401* (2013.01); *A61B 17/0483* (2013.01); *A61B 17/1728* (2013.01); *A61B 17/8052* (2013.01); *A61B 17/808* (2013.01)

(58) Field of Classification Search
CPC ........ D03J 3/00; A61B 17/0485; A61B 17/80; A61B 17/8061; A61B 17/808; A61B 17/0482; A61B 17/0483; A61B 17/1728
See application file for complete search history.

(56) References Cited

U.S. PATENT DOCUMENTS

| 2,416,260 A | 2/1947 | Karle |
| 2,567,408 A | 9/1951 | Soderberg |
| 3,404,707 A | 10/1968 | Feld |
| 3,893,602 A | 7/1975 | Ivy |
| 5,899,920 A | 5/1999 | DeSatnick et al. |
| 5,988,463 A | 11/1999 | DiCarlo et al. |
| 6,086,608 A | 7/2000 | Ek et al. |
| 7,654,422 B2 | 2/2010 | Fujiwara |
| 2006/0069399 A1 | 3/2006 | Weisel |
| 2012/0041484 A1* | 2/2012 | Briganti ............... A61B 17/888 606/232 |
| 2018/0028203 A1 | 2/2018 | Miller et al. |
| 2019/0282224 A1 | 9/2019 | Graul et al. |
| 2020/0046341 A1 | 2/2020 | Skinlo et al. |
| 2021/0007730 A1 | 1/2021 | Hernandez et al. |

(Continued)

FOREIGN PATENT DOCUMENTS

| EP | 0904017 B1 | 2/2004 |
| EP | 2654576 B1 | 12/2011 |

(Continued)

OTHER PUBLICATIONS

International Search Report & Written Opinion for PCT/IB2021/061473 dated Mar. 3, 2022.

*Primary Examiner* — Katherine M Shi
(74) *Attorney, Agent, or Firm* — Kramer & Amado, P.C.

(57) ABSTRACT

A suture threader configured to thread sutures through suture holes in a bone plate, including: a base; a plurality of hooks attached to the base, wherein the plurality of hooks are arranged at positions on the base corresponding the suture holes on the bone plate.

20 Claims, 6 Drawing Sheets

(56) References Cited

U.S. PATENT DOCUMENTS

2021/0052267 A1    2/2021  Phisitkul et al.
2021/0113324 A1    4/2021  Armington et al.

FOREIGN PATENT DOCUMENTS

| EP | 3677195 A1 | 7/2020 |
|---|---|---|
| WO | 2012037149 A1 | 3/2012 |
| WO | 2012112424 A1 | 8/2012 |
| WO | 2013012820 A2 | 1/2013 |
| WO | 2017136394 A2 | 8/2017 |
| WO | 2019005102 A1 | 1/2019 |

\* cited by examiner

SUTURE THREADER FOR BONE PLATE

CROSS-REFERENCE TO RELATED APPLICATIONS

This application claims benefit to U.S. Provisional Patent Application No. 63/131,127 filed on Dec. 28, 2020, the contents of which are hereby incorporated by reference for all purposes as if fully set forth herein.

TECHNICAL FIELD

Various exemplary embodiments disclosed herein relate generally to a suture threader for bone plates.

BACKGROUND

Bone plates are often used in helping to repair broken bones in patients. Such bone plate will typically have a shape tailored to the specific bone being repaired. Further, the bone plate may include screw holes that allow the bone plate to be affixed to the broken bone. Also, the bone plate may be sutured to adjacent soft tissues in order to facilitate the repair to the bone and adjacent soft tissue. The bone plate may have a plurality of suture holes that receive such sutures, and the sutures are then tied off to the bone plate.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a suture threader configured to thread sutures through suture holes in a bone plate, including: a base; a plurality of hooks attached to the base, wherein the plurality of hooks are arranged at positions on the base corresponding the suture holes on the bone plate.

Various embodiments are described, further including a handle connected to the base.

Various embodiments are described, wherein the base has a lower surface shaped to correspond to a shape of the bone plate.

Various embodiments are described, wherein the base is screw targeting guide.

Various embodiments are described, wherein plurality of hooks are wire hooks, wherein the wire hooks include a loop portion configured to receive a suture, wherein the loop portion includes a bend that forms an opening to the loop portion.

Various embodiments are described, wherein plurality of hooks are sliding hooks, wherein the sliding hooks include a body with a hallow opening and shaft in the hollow opening, wherein the shaft slides in the hollow opening to form a loop configured to receive a suture.

Various embodiments are described, wherein plurality of hooks are latch hooks, wherein the latch hooks include a body with a pivot and a latch attached to the body via the pivot, wherein the latch rotates about the pivot to form a loop configured to receive a suture.

Various embodiments are described, further including a plate alignment structure attached to the base configured to engage an edge or hole of the bone plate and align the hooks with the suture holes.

Further various embodiments relate to a suture threader configured to thread sutures through suture holes in a bone plate, including: a base; a plurality of loops attached to the base, wherein the plurality of loops are arranged at positions on the base corresponding the suture holes on the bone plate.

Various embodiments are described, further including a handle connected to the base.

Various embodiments are described, the base has a lower surface shaped to correspond to a shape of the bone plate.

Various embodiments are described, wherein the base is screw targeting guide.

Various embodiments are described, further including a plate alignment structure attached to the base configured to engage an edge or a hole of the bone plate and align the loops with the suture holes.

Further various embodiments relate to a method for threading sutures through suture holes in a bone plate using a suture threader including a base, a plurality of loops or hooks attached to the base, wherein the plurality of loops or hooks are arranged at positions on the base corresponding the suture holes on the bone plate configured to, including: inserting the loops or hooks of the suture threader through suture holes of the bone plate by moving the suture threader towards the bone plate; threading sutures through the loops or the hooks of the suture threader; pulling the sutures through the suture holes by pulling the loops or hooks out of the suture holes by moving the suture threader away from the bone plate; and removing the suture from the loops or hooks.

Various embodiments are described, further including aligning the loops or hooks of the suture threader with the suture holes of the bone plate.

Various embodiments are described, wherein aligning the loops or hooks of the suture threader with the suture holes of the bone plate includes aligning a plate alignment structure with an edge or hole of the bone plate.

Various embodiments are described, wherein threading sutures through the hooks of the suture threader includes threading the sutures through openings in a loop portion on the hook.

Various embodiments are described, wherein the loop portion includes a bend that forms an opening to the loop portion.

Various embodiments are described, wherein the hooks include a body with a hallow opening and shaft in the hollow opening, further comprising sliding the shaft in the hollow opening to form the opening in the loop portion.

Various embodiments are described, wherein the hooks include a body with a pivot and a latch attached to the body via the pivot, further comprising rotating the latch about the pivot to form the opening in the loop portion.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments may be combined with one or more other embodiments to form new embodiments.

Figure 1:
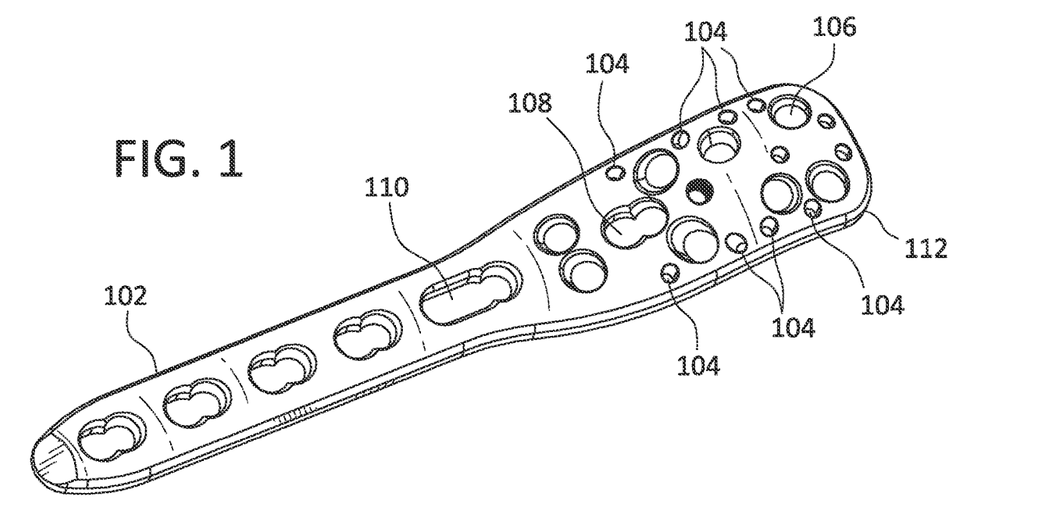
FIG. 1 illustrates an example of a proximal humerus plate that may be used in repairing the humerus.
Figure 2:
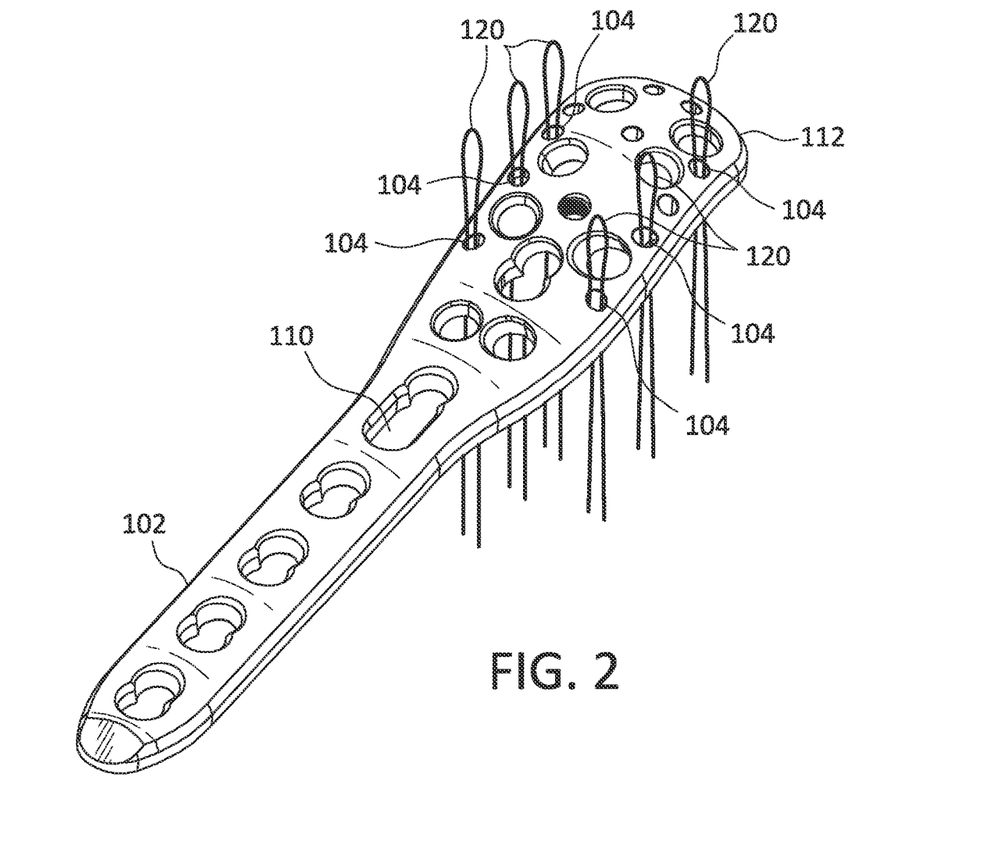
FIG. 2 illustrates the bone plate with sutures inserted through the suture holes.
Figure 3:
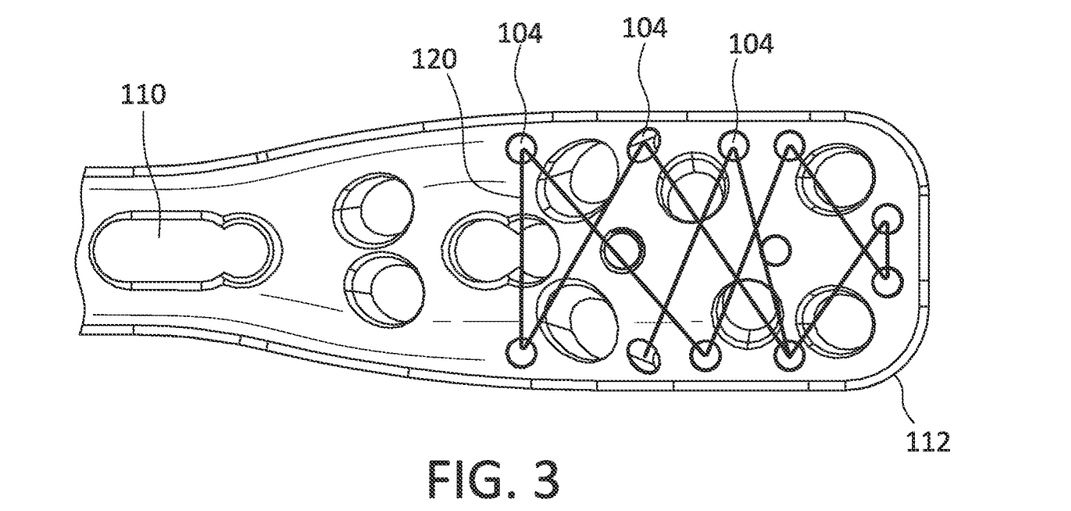
FIG. 3 illustrates an example of the sutures being tied off.

Bone plates are often used by surgeons to repair broken bones. FIG. 1 illustrates an example of a proximal humerus plate that may be used in repairing the humerus. The bone plate 102 may have a head 112 that is curved and shaped to fit onto the end of the humerus. The bone plate 102 includes a plurality of different types of screw holes 106, 108, 110 at various locations. The various screw holes 106, 108, 110 may accept screws so that the bone plate may be secured to the bone. Further, the bone plate 102 may include suture holes 104. The suture holes 104 may receive sutures therethrough. FIG. 2 illustrates the bone plate 102 with sutures 120 inserted through the suture holes 104. One or both ends of the sutures 120 may then be attached to soft tissue (not shown) near the bone plate 102. The sutures 120 may then be pulled through the suture holes 104 so that the attached soft tissue is secured to the bone plate 102 and thus remains in a desired position and/or location, and then the sutures are secured to the bone plate 102 or other sutures 120. FIG. 3 illustrates an example of the sutures 120 being tied off. The sutures may crisscross the bone plate 102 to other suture holes 104 or to other sutures where they are tied off to other sutures 120. Also the sutures 120 may be tied off to various structures of bone plate (not shown).

The bone plate 102 illustrated in FIGS. 1-3 has 10 suture holes. More or fewer suture holes may be found in bone plates 102. Threading the sutures 120 through a number of those suture holes becomes challenging and time consuming as a number of sutures (for example, 6 in FIG. 2) need to be threaded through the bone plate 102. Accordingly, there is a need for a device that helps to facilitate the threading of multiple sutures 120 through suture holes 104 of the bone plate 102. Embodiments of a suture threader will now be described that facilitates the threading of sutures 120 through suture holes 104 of the bone plate 102.

Figure 4:
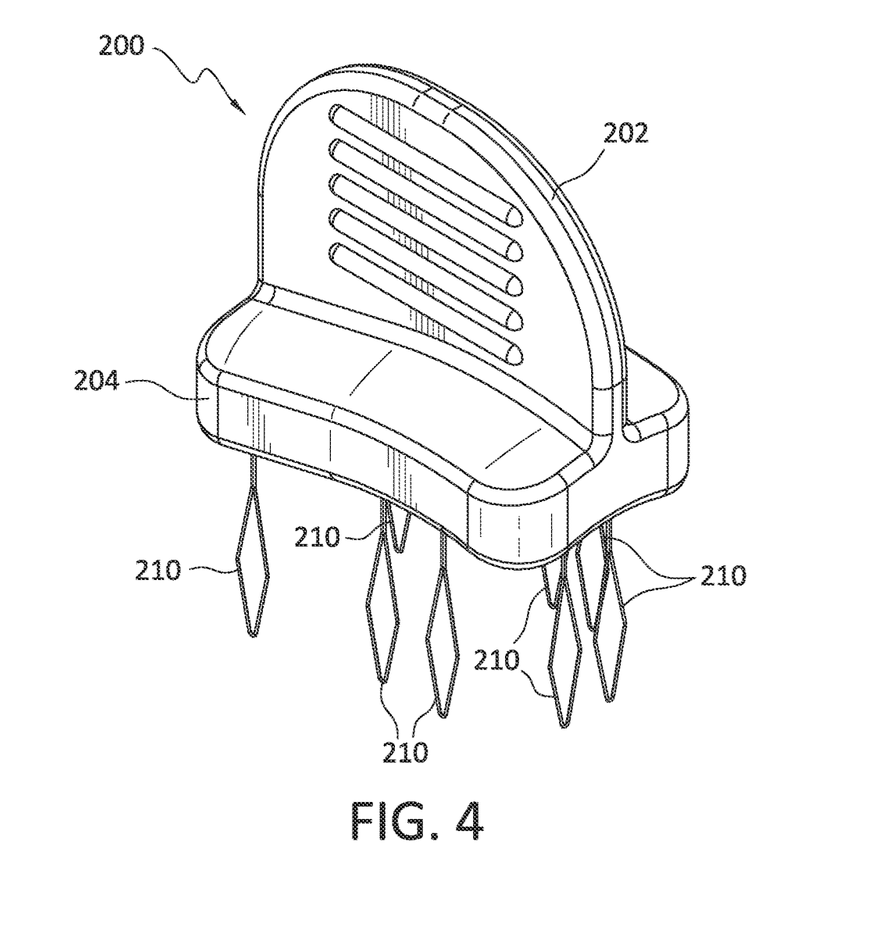
FIGS. 4 and 5 illustrate top perspective and bottom perspective views of a first embodiment of a suture threader.
Figure 5:
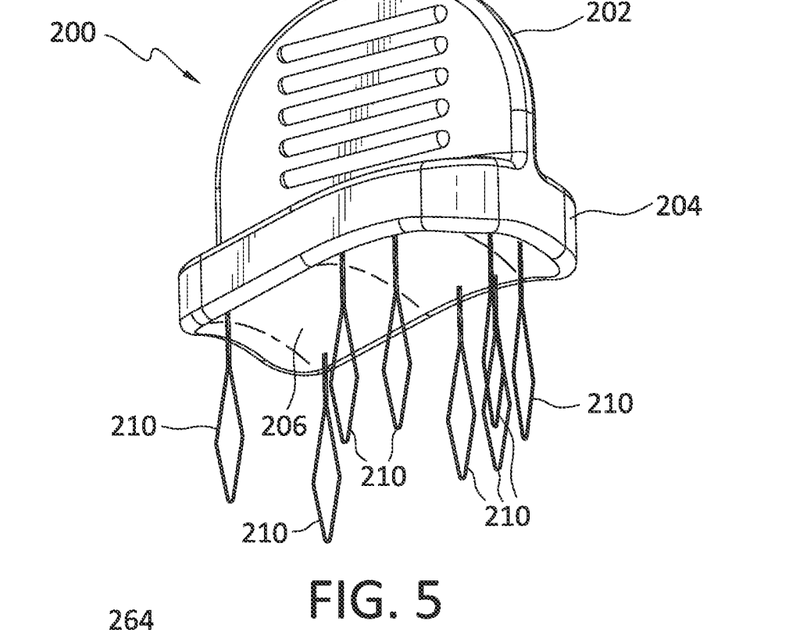

FIGS. 4 and 5 illustrate top perspective and bottom perspective views of a first embodiment of a suture threader. The suture threader 200 includes a handle 202, a base 204, and loops 210. The handle 202 is attached to the base 204 and allows the surgeon to easily grip and move the suture threader 200. The loops 210 are attached to a lower surface 208 of the base 204. The lower surface 208 of the base 204 may be shaped to be complementary to the shape of the associated bone plate 102. For example, the lower surface 208 has a curved concave shape that corresponds to a curved convex shape of the head 112. Further, the loops 210 are attached to the lower surface 208 at locations corresponding to the suture holes 104 on the bone plate 102.

Figure 6:
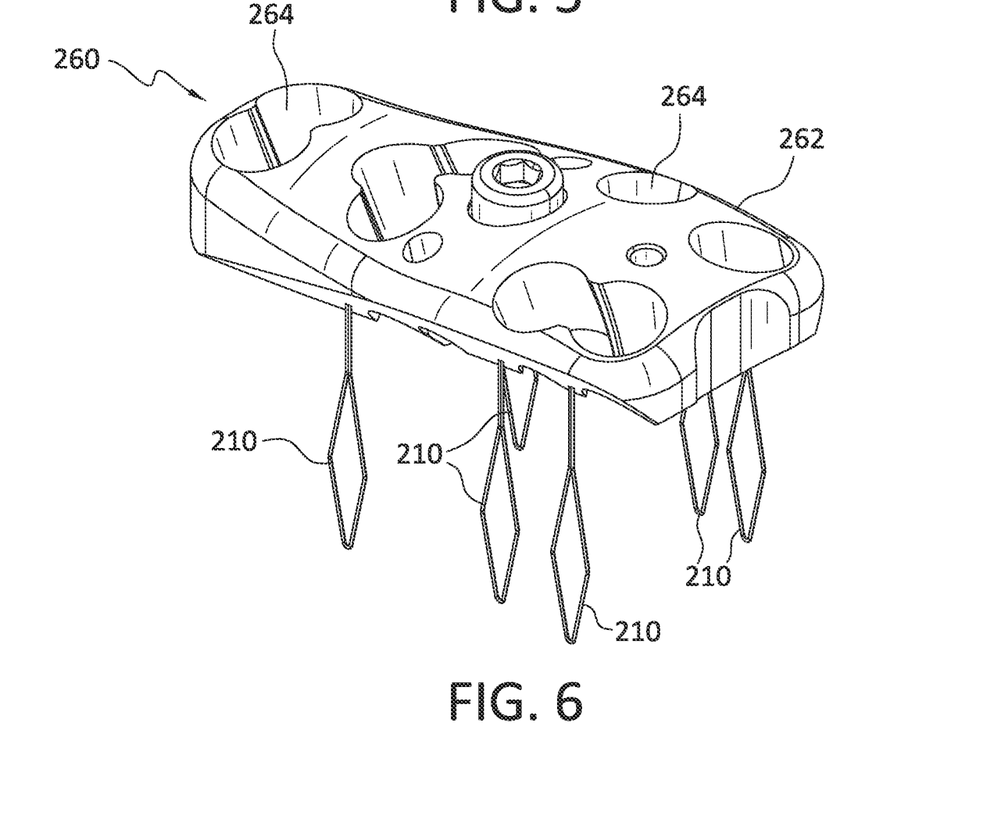
FIGS. 6 and 7 illustrate top perspective and bottom perspective views of a second embodiment of a suture threader.
Figure 7:
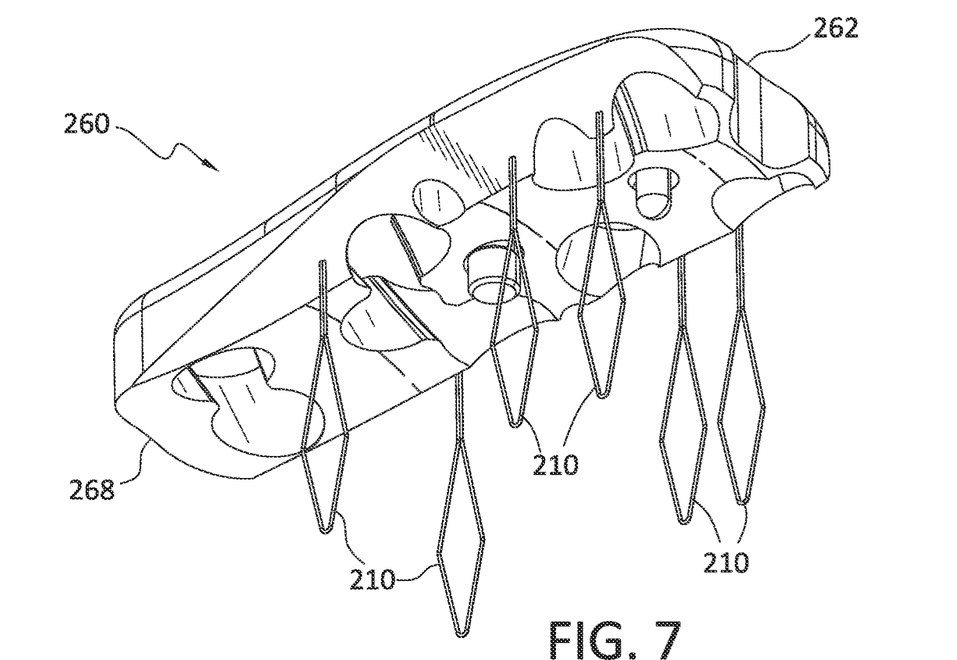

FIGS. 6 and 7 illustrate top perspective and bottom perspective views of a second embodiment of a suture threader. The suture threader 260 includes a screw targeting guide 262 instead of a handle 202 and a base 204 for the first embodiment. The screw targeting guide 262 is attached to the plate by a screw or a snap mechanism, and then drill guides (longer tubes) are attached to holes 264. The drill guide will follow the given trajectory of each hole 264. A pilot hole is drilled in the bone which will later receive screws that locks/fix the plate to the bone. When the plate is fixed to the bone, the screw targeting guide 262 will be removed. As a screw targeting guide 262 may already be used in the installation of the bone plate, it may be adapted as shown to add loops 210 to also assist in the threading of the sutures. The loops 210 are attached to a lower surface 268 of the screw targeting guide 262. The lower surface 268 of the screw targeting guide 262 may be shaped to be complementary to the shape of the associated bone plate 102. For example, the lower surface 268 has a curved concave shape that corresponds to a curved convex shape of the head 112. Further, the loops 210 are attached to the lower surface 28 at locations corresponding to the suture holes 104 on the bone plate 102.

Figure 8:
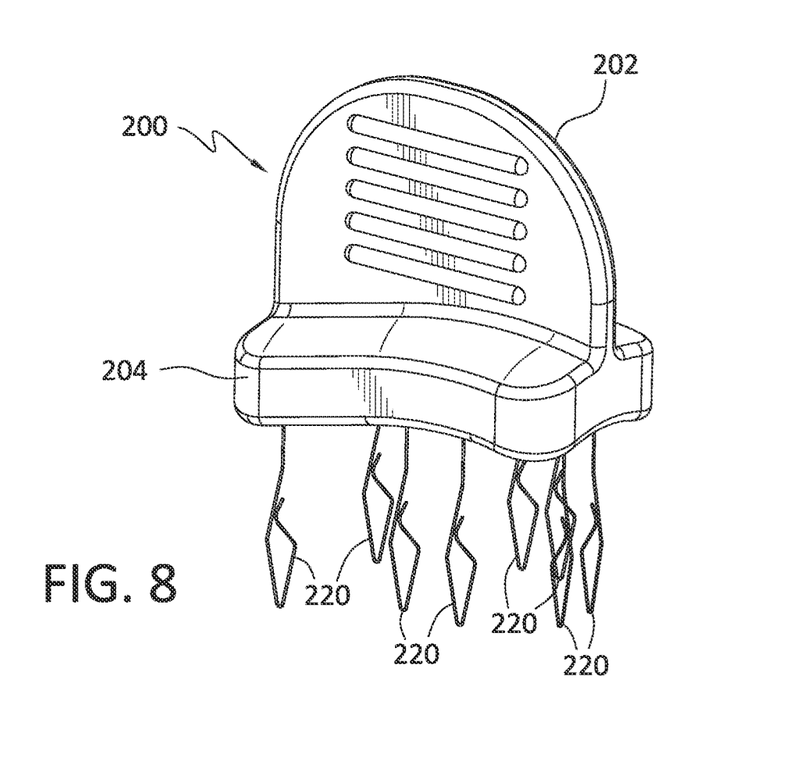
FIG. 8 illustrates a third embodiment of a suture threader.

FIG. 8 illustrates a third embodiment of a suture threader. The suture threader 200 of FIG. 8 is identical to the suture threader of FIGS. 4 and 5 except that a wire hook 220 is used instead of the loop 210. Other types of hooks and loops may also be attached to the bottom surface 208 of the suture threader 200. Such various loops and hooks will now be described.

Figure 9:
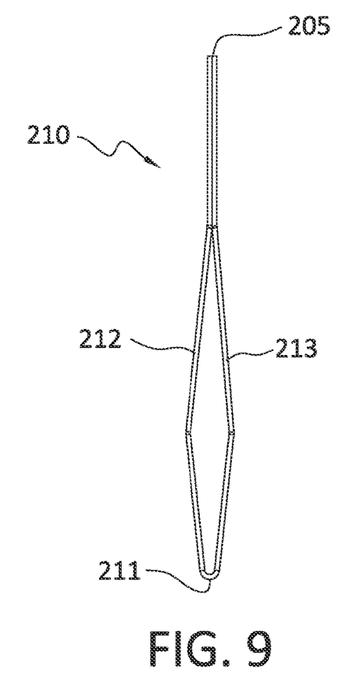
FIG. 9 illustrates an embodiment of the loop.

FIG. 9 illustrates an embodiment of the loop 210. The loop 210 may be made of a wire 212 that is formed into a looped portion 213 that is configured to accept a suture therethrough. The looped portion 213 has an end 211 that will engage the suture 120 and pull the suture 120 through the suture hole 104 when the suture threader 200 is used. Also, the end 211 is narrow and sized that it may enter the suture hole 104. As the loop 210 is made of wire, it is flexible, and hence the loop 210 may be pushed through the suture hole 104 where the loop portion 213 collapses as it passes through the suture hole 104. Accordingly, the wire 212 or other material used to form the loop 210 will be flexible enough to allow loop portion 213 to collapse when passing through the suture hole 104, but also rigid enough so that the loop 210 may be pushed through the suture hole. The loop 210 also includes a loop attachment 215 which may be an end of the loop 210 opposite the end 211 wherein the loop attachment 215 attaches to the lower surface 208.

Figure 10:
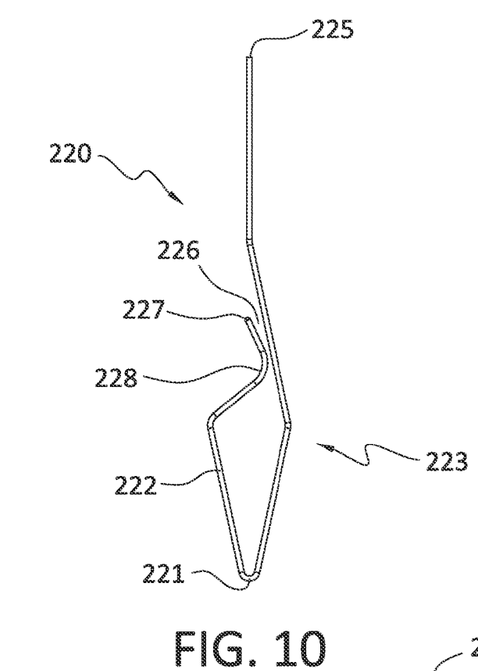
FIG. 10 illustrates an embodiment of an embodiment of the wire hook.

FIG. 10 illustrates an embodiment of an embodiment of the wire hook 220. The wire hook 220 may be made of a wire 222 that is formed into a looped portion 223 that is configured to accept a suture therethrough. The looped portion 223 has an end 221 that will engage the suture 120 and pull the suture 120 through the suture hole 104 when the suture threader 200 is used. The looped portion 213 includes a bend 228 just before a loop end 227 that forms an opening 226. The opening 226 allows the surgeon to easily pass the suture through the opening into the looped portion 223. This facilitates the insertion of the sutures into the hook 220. Also, the end 221 is narrow and sized that that it may enter the suture hole 104. As the wire hook 220 is made of wire, it is flexible, and hence the wire hook 220 may be pushed through the suture hole 104 where the loop portion 223 collapses as it passes through the suture hole 104. Accordingly, the wire 232 or other material used to form the wire hook 220 will be flexible enough to allow loop portion 223 to collapse when passing through the suture hole 104, but also rigid enough so that the wire hook 220 may be pushed through the suture hole. The wire hook 220 also includes a hook attachment 225 which may be an end of the wire hook 220 opposite the end 221 wherein the hook attachment 225 attaches to the lower surface 208.

Figure 11:
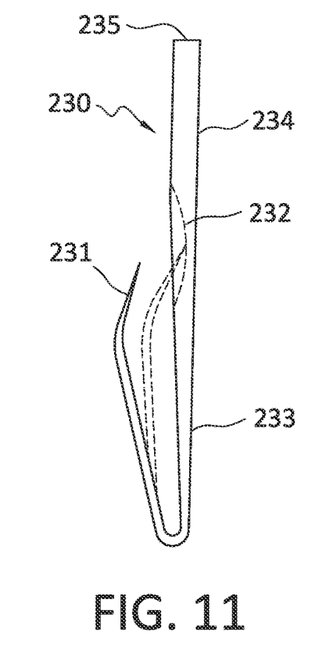
FIG. 11 illustrates an embodiment of an embodiment of a flexible hook.

FIG. 11 illustrates an embodiment of an embodiment of a flexible hook 230. The flexible hook 230 includes a shaft 234 connected to a looped portion 233 that is configured to accept a suture therethrough. The looped portion 233 has an end 231 that will engage the suture 120 and pull the suture 120 through the suture hole 104 when the suture threader 200 is used. The looped portion 233 includes a flexible portion 231 that has an end that rests in a recess 232 in the shaft 234. The flexible portion 231 may be opened to allow the surgeon to easily pass the suture through the resulting opening into the looped portion 233. This facilitates the insertion of the sutures into the flexible hook 230. Also, the end 231 is narrow and sized that that it may enter the suture hole 104. As the flexible hook 230 includes the flexible portion 231, the flexible hook 230 may be pushed through the suture hole 104 where the loop portion 233 collapses as it passes through the suture hole 104. Accordingly, the material used to form the flexible portion 231 will be flexible enough to allow loop portion 233 to collapse when passing through the suture hole 104, but also rigid enough so that the flexible hook 230 may be pushed through the suture hole. The flexible hook 230 also includes a hook attachment 235 which may be an end of the shaft 234 that attaches to the lower surface 208.

Figure 12:
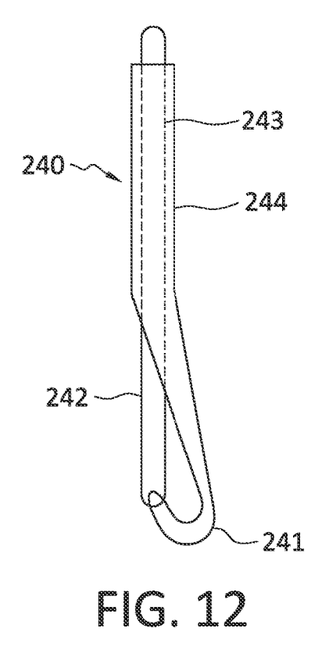
FIG. 12 illustrates an embodiment of an embodiment of a sliding hook.

FIG. 12 illustrates an embodiment of an embodiment of a sliding hook 240. The sliding hook 240 includes a body 244 and a shaft 242. The body 244 includes a hook 241 at the end. The body 244 also includes a hollow opening 243 that accepts the shaft 242. The shaft 242 extend downward and comes into contact with the end of the hook 241 to form a loop that is configured to accept a suture therethrough. The shaft 242 may move relative to the body 244 by sliding in the hollow opening 243, which causes the loop to open and close to allow sutures to easily be inserted or removed from the loop. The hook 241 will engage the suture 120 and pull the suture 120 through the suture hole 104 when the suture threader 200 is used. The hook 241 is sized to be able to be inserted through the suture hole 104. The relative movement between the shaft 242 and the body 244 may be facilitating in various ways. The shaft 242 may be able to move freely in the hollow opening 243 and can be raised to insert or remove the suture from the hook 241. In this case gravity may be used to cause the shaft 242 to move downward to close the loop. In other embodiments there may be a biasing member that biases the shaft 242 into the closed position. If the shaft 242 is attached to the lower surface 208, then the body 244 may be moved to open and close the loop. If the body 244 is attached to the lower surface 208, then the shaft 242 may be moved to open and close the loop. In yet another embodiment, the shafts 242 in each sliding hook 240 may be attached to a mechanical actuator that has a button or other element that allows the surgeon to open and close the hook by actuating the button or other element that moves the shafts up and down.

Figure 13:
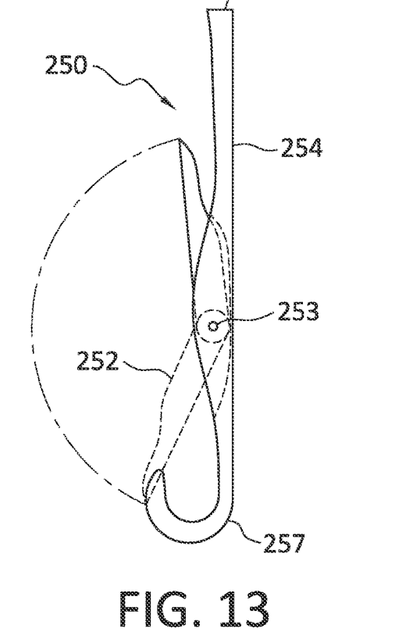
FIG. 13 illustrates an embodiment of an embodiment of a latch hook.

FIG. 13 illustrates an embodiment of an embodiment of a latch hook 250. The latch hook 250 includes a body 254. The body 254 includes a hook 251 at the end. A latch 252 is attached to the body 254 using a pivot 253. The latch 252 rotates about the pivot 253. The latch 252 when rotated to be in contact with the hook 251 forms a loop that is configured to accept a suture therethrough. As the latch 252 rotates the loop opens and closes to allow sutures to easily be inserted or removed from the loop. The hook 251 will engage the suture 120 and pull the suture 120 through the suture hole 104 when the suture threader 200 is used. The hook 251 is sized to be able to be inserted through the suture hole 104. The latch 252 may be opened and closed by the surgeon moving it. Further, the latch 252 may be biased towards the hook 251 to keep the loop generally closed. Further, the latch hook 250 may include a hook attachment 255 connected to the lower surface 208.

Figure 14:
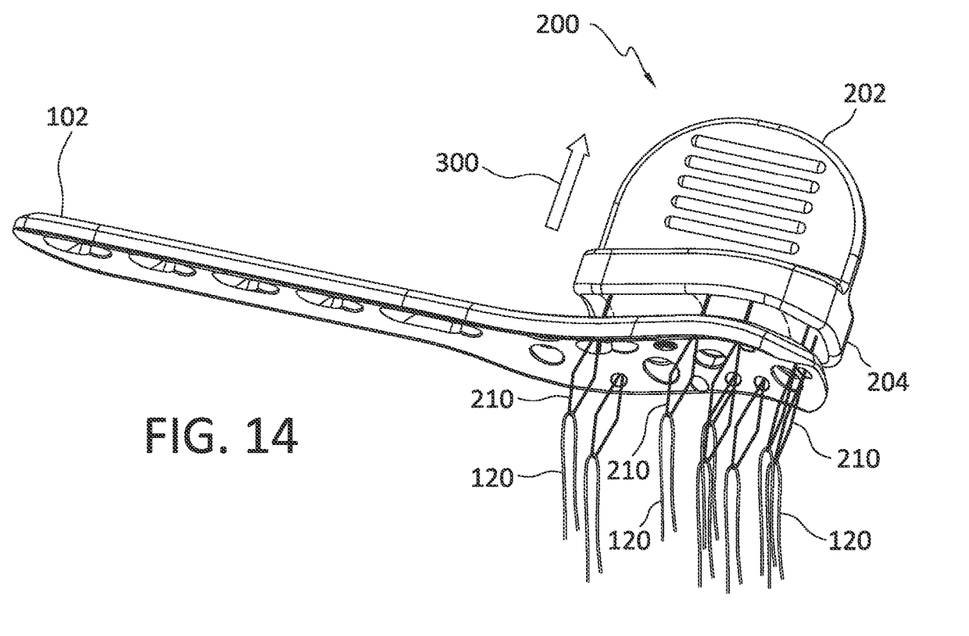
FIGS. 14 and 15 illustrate how the suture threader may be used.
Figure 15:
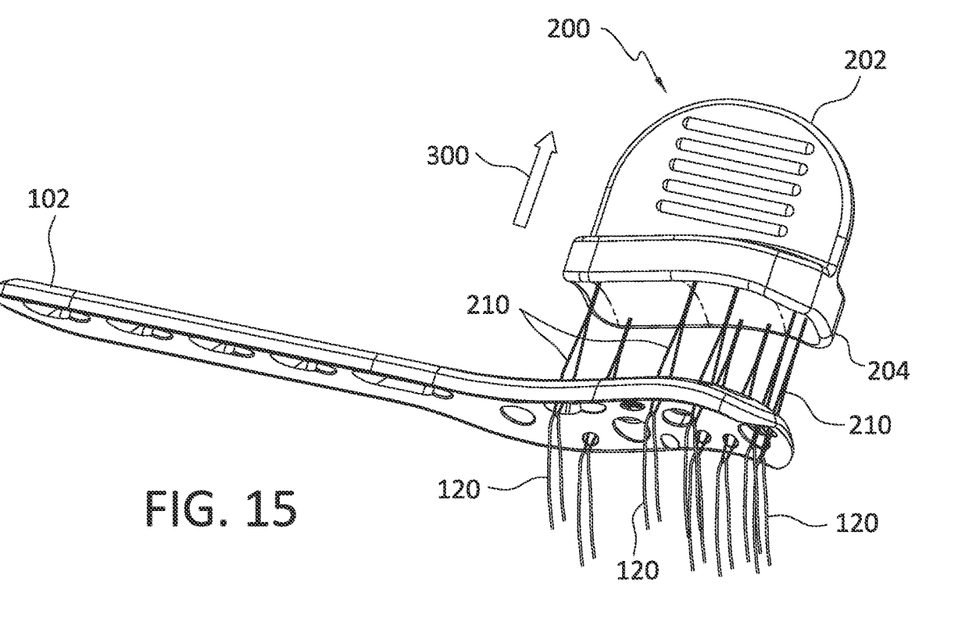

FIGS. 14 and 15 illustrate how the suture threader may be used. To begin with the loops 210 of the suture threader 200 are aligned with the suture holes 104, and the suture threader 200 is pushed towards the bone plate 102 so that the loops 210 are pushed through the suture holes 104. With the loops 210 through the suture holes 104, sutures 120 may be threaded through the loops 210. Next, the suture threader 200 is pulled upward 300 so that the loops 210 and the sutures 120 are pulled up through the suture holes 104 (for example, as shown in FIG. 2). At that point the sutures 120 may be pulled out of the loop 120. Alternatively, the suture threader may include any of the hooks 220, 230, 240, 250 instead of the loop 210.

When the threader includes any of the hooks 220, 230, 240, 250, the sutures 120 may be easily inserted and removed from the hooks. Such operation means that the sutures do not need to be threaded into or out of the loops formed by the hooks.

In other embodiments the suture threader, may include an plate alignment structure. Such alignment structure may include a rod or rods extending from the suture threader that engage screw holes of the plate to align the loops or hooks of the suture threader with the suture holes. Alternatively, there may be guides on the edges of the suture threader 200 that align with edges of the bone plate to align the loops or the hooks with the suture holes.

While the techniques described herein may be implemented and have been described in connection with the various embodiments of the various figures, it is to be understood that other similar embodiments may be used or modifications and additions may be made to the described embodiments without deviating therefrom. For example, it should be appreciated that the steps disclosed above may be performed in the order set forth above, or in any other order as desired. Further, one skilled in the art will recognize that the techniques described in the present application may apply to any environment. Therefore, the techniques described herein should not be limited to any single embodiment, but rather should be construed in breadth and scope in accordance with the appended claims.

What is claimed is:

1. A system configured to thread sutures through suture holes in a bone plate, comprising:
    a bone plate comprising a plurality of suture holes; and
    a suture threader comprising:
        a base;
        a plurality of hooks attached to the base, wherein the plurality of hooks are arranged at positions on the base corresponding to the plurality of suture holes on the bone plate.

2. The system of claim 1, further comprising a handle connected to the base.

3. The system of claim 1, wherein the base has a lower surface shaped to correspond to a shape of the bone plate.

4. The system of claim 1, wherein the base is a screw targeting guide.

5. The system of claim 1, wherein the plurality of hooks are wire hooks, wherein the wire hooks include a loop portion configured to receive a suture, wherein the loop portion includes a bend that forms an opening to the loop portion.

6. The system of claim 1, wherein the plurality of hooks are sliding hooks, wherein the sliding hooks include a body with a hollow opening and a shaft in the hollow opening, wherein the shaft slides in the hollow opening to form a loop configured to receive a suture.

7. The system of claim 1, wherein the plurality of hooks are latch hooks, wherein the latch hooks include a body with a pivot and a latch attached to the body via the pivot, wherein the latch rotates about the pivot to form a loop configured to receive a suture.

8. The system of claim 1, further comprising a plate alignment structure attached to the base configured to engage an edge or hole of the bone plate and align the hooks with the plurality of suture holes.

9. A system configured to thread sutures through suture holes in a bone plate, comprising:
    a bone plate comprising a plurality of suture holes; and
    a suture threader comprising:
        a base;
        a plurality of loops attached to the base, wherein the plurality of loops are arranged at positions on the base corresponding to the plurality of suture holes on the bone plate.

10. The system of claim 9, further comprising a handle connected to the base.

11. The system of claim 9, the base has a lower surface shaped to correspond to a shape of the bone plate.

12. The system of claim 9, wherein the base is a screw targeting guide.

13. The system of claim 9, further comprising a plate alignment structure attached to the base configured to engage an edge or a hole of the bone plate and align the loops with the plurality of suture holes.

14. A method for threading sutures through suture holes in a bone plate using a suture threader including a base, a plurality of loops or hooks attached to the base, wherein the plurality of loops or hooks are arranged at positions on the base corresponding to the suture holes on the bone plate, comprising:
    inserting the loops or hooks of the suture threader through suture holes of the bone plate by moving the suture threader towards the bone plate;
    threading sutures through the loops or the hooks of the suture threader;
    pulling the sutures through the suture holes by pulling the loops or hooks out of the suture holes by moving the suture threader away from the bone plate; and
    removing the suture from the loops or hooks.

15. The method of claim 14, further comprising aligning the loops or hooks of the suture threader with the suture holes of the bone plate.

16. The method of claim 15, wherein aligning the loops or hooks of the suture threader with the suture holes of the bone plate includes aligning a plate alignment structure with an edge or hole of the bone plate.

17. The method of claim 14, wherein threading the sutures through the hooks of the suture threader includes threading the sutures through openings in a loop portions on the hooks.

18. The method of claim 17, wherein at least one loop portion of the loop portions includes a bend that forms an opening to the at least one loop portion.

19. The method of claim 17, wherein the hooks include a body with a hollow opening and a shaft in the hollow opening, further comprising sliding the shaft in the hollow opening to form the opening in the loop portion.

20. The method of claim 17, wherein the hooks include a body with a pivot and a latch attached to the body via the pivot, further comprising rotating the latch about the pivot to form the opening in the loop portion.

* * * * *